United States Patent [19]

Tsuchiya et al.

[11] 3,978,091

[45] Aug. 31, 1976

[54] 2,4-DIMETHYL-3-CARBOXYANILIDOFURAN COMPOUNDS

[75] Inventors: Shigeru Tsuchiya, Shimizu; Yoshitaka Suda, Shizuoka; Isao Chiyomaru, Shimizu; Seigo Kawada, Fujieda; Kiyoshi Takita, Kitawaki-Shimizu, all of Japan

[73] Assignee: Kumiai Chemical Industry Co., Ltd., Tokyo, Japan

[22] Filed: Feb. 27, 1974

[21] Appl. No.: 446,430

[30] Foreign Application Priority Data

Mar. 1, 1973, Japan............... 48-24645
Mar. 2, 1973, Japan............... 48-24870
Aug. 25, 1973 Japan............... 48-95556

[52] U.S. Cl. ............................ 260/347.3; 424/285
[51] Int. Cl.$^2$ ............................ C07D 307/66
[58] Field of Search ............................ 260/347.3

[56] References Cited
FOREIGN PATENTS OR APPLICATIONS
893,676    2/1972    Canada

*Primary Examiner*—Henry R. Jiles
*Assistant Examiner*—Bernard Dentz
*Attorney, Agent, or Firm*—Oblon, Fisher, Spivak, McClelland & Maier

[57] ABSTRACT

2,4-Dimethyl-3-carboxanilido- or naphthyl amidofuran of the formula

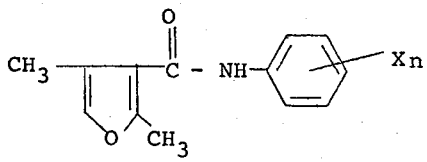

or

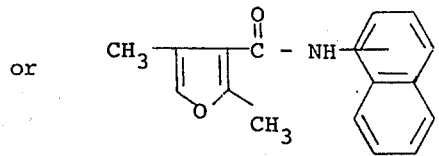

involving the reaction of

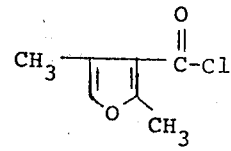

with

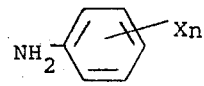

or

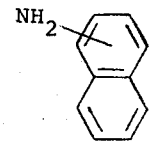

wherein X represents a halogen atom, an alkyl group, hydroxyl group, an alkoxyl group, an alkenyloxy group, trifluoromethyl group, phenyl group, cyano group, acetyl group, a metal substituted hydroxy group or a combination thereof are useful as agricultural germicides, fungicides, insecticides and nematodicides.

8 Claims, No Drawings

2,4-DIMETHYL-3-CARBOXYANILIDOFURAN COMPOUNDS

BACKGROUND OF THE INVENTION

Field of the Invention

This invention relates to a process for preparing 2,4-dimethyl-3-carbonxanilido- or naphthylamido-furan of the formula (II) or (III)

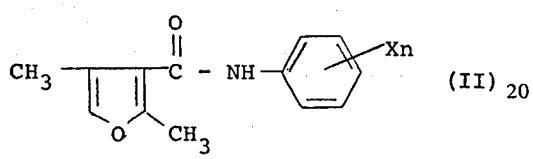

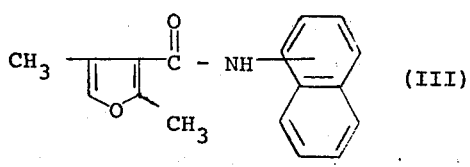

wherein X represents a halogen atom, an alkyl group, hydroxyl group, an alkoxyl group, an alkenyloxy group, an alkynyloxy group, trifluoromethyl group, phenyl group, cyano group, acetyl group, a metal substituted hydroxyl group or a combination thereof and n represents the integers 1 to 3. These compounds are useful as agricultural germicides, fungicides, insecticides and nematodicides.

SUMMARY OF THE INVENTION

It is an object of this invention to provide a process for preparing 2,4-dimethyl-3-carboxanilido- or carboxanaphthylamido-furan which is useful as an agricultural germicide, fungicide, insecticide and nematodicide.

These and other objects of this invention as will hereinafter become more readily understood by the following description can be attained by reacting a 2,4-dimethyl-3-furoylhalide with naphthylamine or a substituted aniline of the formula (I)

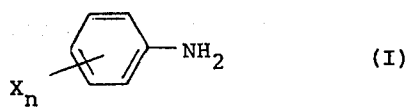

wherein X represents a halogen atom, an alkyl group, hydroxyl group, an alkoxyl group, an alkenyloxy group, an alkynyloxy group, trifluoromethyl group, phenyl group, cyano group, acetyl group, alkali metal oxide group or a combination thereof and n represents an integer of 1 to 3 in the presence of an dehydrohalogenating agent (base), to form 2,4-dimethyl-3-carboxanilido- or carboxanaphthalamido-furan of the formula (II) or (III) above.

Reaction of 2,4-dimethyl-3-hydroxycarboxanilido-furan of the formula (IV)

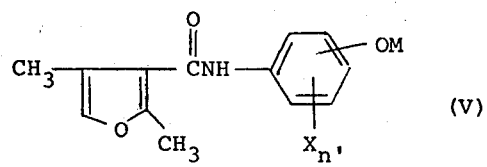

with an alkali metal hydroxide, MOH, or an alkali metal gives 2,4-dimethyl-3-carboxanilido-furan having the formula (V)

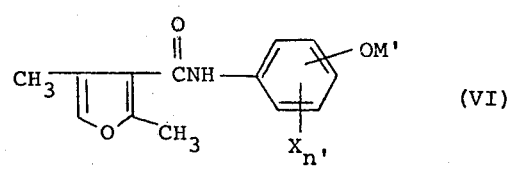

wherein M represents an alkali metal, X is defined above, and n' is 0 or 1.

Reaction of 2,4-dimethyl-3-carboxanilido-furan (VII)

$$CH_3 \text{—furan—} CNH \text{—} C_6H_3(OM')(X_{n'}) \quad (VI)$$

with an alkylhalide, an alkenylhalide or an alkynylhalide of the formula:

R'Y  (VII)

wherein R' represents an alkyl group, an alkenyl group, or an alkynyl group and Y represents a halogen atom yields the 2,4-dimethyl-3-carboxanilido-furan (IX)

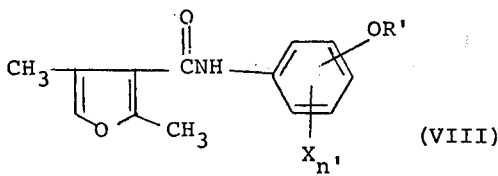

(VIII)

X is defined as above and M' represents hydrogen or an alkali metal. The presence of base is required if M' = H.

Reaction of 2,4-dimethyl-3-carboxanilido-furan of the formula

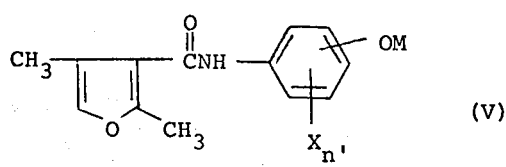

(V)

with an inorganic or organic metal salt of the formula

(IX)

wherein M'' represents a metal atom (excluding an alkali metal atom) and X' represents a halogen atom, an inorganic or organic acid residual group, n'' represents an integer defined by the valence of the metal atom or the ratio of the valences of M'' and X', produces the 2,4-dimethyl-3-carboxanilido-furan of the formula

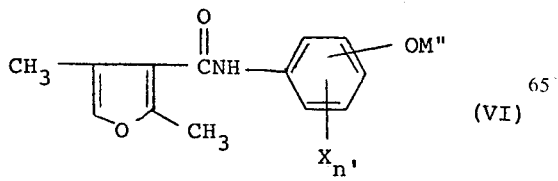

(VI)

In the above formulas, the radical X is halogen, such as chloro or bromo; alkyl, such as the lower alkyls and in particular the $C_{1-10}$ alkyls; hydroxyl; alkoxyl, such as the lower alkoxyls, and in particular the $C_{1-10}$ alkoxyls; the alkenyloxys, such as the lower alkenyloxys, and in particular the $C_{3-10}$ alkenyloxys; the alkynyloxys, such as the lower alkynyloxys and in particular the $C_3$-$C_1$ alkynyloxys; trifluoromethyl; phenyl; cyano; acetyl; metal substituted hydroxyl, such as K, Li, Na, Ca, Cu, Mg, Sn, Fe and Zn substituted or a combination thereof.

DETAILED DESCRIPTION OF THE PREFERRED EMBODIMENTS

The method of preparing 2,4-dimethyl-3-carbox-anilido- or carboxanaphthylamido-furans will now be illustrated in greater detail.

Preparation 1

2,4-Dimethyl-3-carboxanilido- or carboxanaph-thylamido-furan (II) or (III) is prepared by reacting a 2,4-dimethyl-3-furoyl halide with naphthylamine or a substituted aniline (I) in the presence of a dehydrohalogenating agent (base).

Preparation 2

2,4-Dimethyl-3-carboxanilido-furan (V) is prepared by reacting 2,4-dimethyl-3-hydroxycarboxanilido-furan (IV) with an alkali metal or an alkali metal hydroxide.

Preparation 3

2,4-Dimethyl-3-carboxanilido-furan (VIII) is prepared by reacting the 2,4-dimethyl-3-carboxanilido-furan (VI) with an alkylhalide, an alkenylhalide or an alkynylhalide (VII) in the presence of a base, if M' is hydrogen in formula (VI).

Preparation 4

2,4-Dimethyl-3-carboxanilido-furan (VI) is prepared by reacting the 2,4-dimethyl-3-carboxanilido-furan (V) with a metal salt of an inorganic or organic acid of general formula (IX).

The preparation of 3-carboxanilidio-furans has been disclosed in Chemical Abstract Vol. 73, 98933 m and Vol. 73, 108740 n and German Patent Application Publication No. 2.006,471 and 2,006,472.

Furan-3-carboxamides having the formula

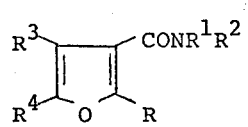

are synthesized by reacting

with

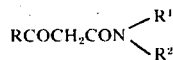

in the presence of aluminum chloride catalyst in a solvent, e.g., benzene. Herein R, $R^1$, $R^3$ and $R^4$ represent hydrogens or alkyl groups, and $R^2$ represents an alkyl or an aryl group. The furan-3-carboxamides have a germicidal effect on agricultural bacteria such as bean Rust, barley Loose smut and an insecticidal effect on cockroaches and mosquitos. They also possess nematocidal effects.

The 2,4-dimethyl-3-carboxanilido-furans have not heretofore been disclosed and are novel compounds. They possess superior germicidal effect and an excellent antimicrobial spectrum as compared to the compounds disclosed in German Patent Application Publication No. 2,006,471 and No. 2,006,472 or to such conventional germicidal compounds as 5,6-dihydro-2-methyl-1,4-oxtaine-3-carboxanilide or the oxygenated compounds thereof. 2,4-Dimethyl-3-carboxanilido-furan and 2,4-dimethyl-b 3-carboxanaphthylamido-furan (II) and (III) are effective in inhibiting diseases such as sheath blight and bacterial leaf blight in rice, rust, in barley and wheat; leaf blight in tomatoes; anthracenose in cucumbers; stem rot in haricots; alternaria leaf spot and powdery mildew in apples; phoma rot in oranges; and Rhizoctonia, Fusarium and Verticillium wilt and Fusarium wilt in tomatoes. They are also effective in preventing seed diseases, such as Rhizoctonia Fusarium, barley smut, and soil diseases.

In the series of compounds (II), the 2,4-dimethyl-3-(m-substituted carboxanilido)furans have the highest germicidal effect. They especially impart an excellent effect for inhibition and remedy of sheath blight in rice.

The compounds can be applied not only by scattering or sprinkling, but also by water surface application or soil treatment. This effect lasts for a long period of time. The compounds are permeable in the plants. They exhibit very lox toxicity to warm blooded animals. In fact, no toxicity disorders were found when mice were administered an oral dose of 1,000 mg/kg of body weight.

The preparation of the compounds will now be illustrated in detail below.

In Preparation (1), the substituted anilines (I) can be o,m,p-toluidine; 2,3,-, 2,4-, 2,5-, 2,6-, 3,4-, or 3,5-xylidine; 2,4,5- or 2,4,6-trimethylaniline; 2-ethylaniline, 3-ethylaniline; 2,6-diethylaniline; 3-isopropylaniline; o,m,p-anisidine; 2,4-, 2,5- or 3,5-dimethoxyaniline; om,p-phenetidine; o,m,p-propoxyaniline; o,m,p-isopropoxyaniline; o,m,p-butoxyaniline; o,m,p-sec-butoxyaniline; o,m,p-t-butoxyaniline; o,m,p-hexyloxyaniline; o,m,p-isohexyloxyaniline; o,m,p-octyloxyaniline; o,m,p-allyloxyaniline; o,m,p-propargyloxyaniline; 4-methyl-2-methoxyaniline: o,m,p-hydroxyaniline; o,m,p-chloroaniline; o,m,p-bromoaniline; 2,3-, 2,4-, 2,5-, 2,6-, 3,4- or 3,5-dichloroaniline; 2,4,5- or 2,4,6-trichloroaniline; 2,4,6-tribromoaniline; 2-methyl-3-chloroaniline; 2-methyl-4-chloroaniline; o,m,p-trifluoromethylaniline; 2-chloro-5-trifluoromethylaniline; $\alpha,\beta$-naphthylamine; o,p-phenylaniline; 2-ethoxy-5-methylaniline; 2-propoxy-5-methylaniline; 2-hydroxy-3-methylaniline; p-cyanoaniline; and p-acetylaniline.

The dehydrohalogenating agents can be organic or inorganic bases such as the said anilines, tertiary amines, e.g., triethylamine, trimethylamine, dimethylaniline, diethylaniline, pyridine, N-methylmorpholine, etc. or sodium carbonate, potassium carbonate, sodium bicarbonate, etc. The solvent can by any which is inert to 2,4-dimethyl-3-furoylhalide or the anilines (I), such as benzene, toluene, xylene, acetone, methylethyl ketone, ether, dioxane, acetonitrile, dichloroethane, etc.

The reaction can be performed smoothly at room temperature, but the reaction time can be shortened by heating. In Preparation (2), suitable alkali metal hydroxides, MOH, include sodium hydroxide, potassium hydroxide, lithium hydroxide, or the like. Suitable solvents include water, alcohols, e.g., methanol, ethanol-ketones, e.g., acetone- aromatic hydrocarbons, e.g., benzene, toluene, xylene- ethers, acetonitrile, etc.

When an alkali metal is used, the reaction is conducted either in a mixed solvent consisting of anyhdrous alcohol and an aromatic hydrocarbon or ether, or in an aromatic hydrocarbon or ether alone. It is possible to react the alkali metal with an alcohol to prepare an alkoxide which is used for the reaction. Sodium nitrate can also be used.

In Preparation (3), the alkylhalides (VII) can be methylbromide, ethylbromide, propyliodide, isopropyliodide, butylchloride, isobutylbromide, sec-butyliodide, t-butyl-bromide, amylbromide, amylchloride, heptyliodide, octyliodide, allylbromide, propargylchloride, etc.

Suitable dehydrohalogenating agent (bases) can be the tertiary amines and inorganic carbonates used in Preparation (1).

Suitable solvents include those used in Preparation (1). When M in formula (V) is an alkali metal, suitable solvents will include water, alcohols, or ketones (e.g., acetone). The reaction can be performed at room temperature, however, the reaction time can be shortened by heating. In Preparation (4) the inorganic salts having the formula (IX) can be calcium chloride, barium acetate, cupric sulfate, magnesium chloride, zinc nitrate, manganese sulfate, ferric chloride, ferrous chloride, cobalt acetate, nickel sulfate, stannous chloride, lead acetate, etc. The solvents can be water and alcohols.

Having now generally described the invention, a further understanding can be obtained by reference to the following examples which are provided for purposes of illustration only and are not to be construed as limiting of the invention unless otherwise so specified.

EXAMPLE 1

Preparation of 2,4-dimethyl-3-(2-methylcarboxanilido)furan

In 100 ml of benzene with stirring and cooling with ice water were dissolved 10.7 g (0.1 mole) of o-toluidine and 10.1 g (0.1 mole) of triethylamine. To this solution was added dropwise 20 ml of a benzene solution containing 15.8 g (0.1 mole) of 2,4-dimethyl-3-furoylchloride with stirring. As it is an exothermic reaction, it was kept at 20°C below the inner temperature. After the addition, the cooling bath was removed and the reaction was continued at room temperature for 2 hours. The reaction mixture was washed successively with water, dilute hydrochloric acid, water, 5% aqueous sodium bicarbonate and water. The product was dehydrated with anhydrous sodium sulfate. The benzene was stripped off and the resulting solid was recrystallized from a mixture of benzene and n-hexane (1:2) to obtain 18.4 g of pink fibrile crystals having a melting point of 130°–132°C. The yield was 80.3%.

EXAMPLE 2

Preparation of 2,4-dimethyl-3-(3-methylcarboxanilido)furan

To a solution of 10.7 g (0.1 mole) of m-toluidine in 70 ml of acetone was added 8.4 g (0.1 mole) of sodium bicarbonate with stirring. The mixture was cooled with ice water.

To this mixture 20 ml of an acetone solution containing 15.8 g (0.1 mole) of 2,4-dimethyl-3-furoylchloride was added dropwise. A slight exothermic reaction was noted and carbon dioxide gas was generated. After the addition, the cooling bath was removed and the reaction was continued room temperature for 2 hours. The reaction mixture was poured into water and the precipitated solid product was filtered, dried, and recrystallized from a mixture of benzene and n-hexane (1:2), to obtain 20.4 g of pale yellow crystals with melting point 117.5°–118.5°C. The yield was 88.2%. IR cm$^{-1}$ (KBr-Tablet) $\nu_{NH}$3250(S), $\nu_{co}$1650(S), 1660(S).

EXAMPLE 3

Preparation of 2,4-dimethyl-3-(3,5-dimethylcarboxanilido)furan

In 120 ml of ether with stirring and cooling with ice water were dissolved 12.1 g (0.1 mole) of 3,5-xylidine and 7.9 g (0.1 mole) of pyridine. To this solution was added dropwise 20 ml of an ether solution of 15.8 g (0.1 mole) of 2,4-dimethyl-3-furoylchloride with stirring. As it is an exothermic reaction, it was kept 20°C below the inner temperature. After the addition, the reaction was continued for 2 hours at room temperature. After the reaction, the product was washed successively with water, dilute hydrochloric acid, water, 5% aqueous sodium bicarbonate and water; it was dehydrated with anhydrous sodium sulfate. The ether was stripped off and the solid product was recrystallized from methanol to produce 19.6 g of pale yellow flaky crystals, melting point 149°–152°C. The yield was 80.6%.

EXAMPLE 4

Preparation of 2,4-dimethyl-3-(2-ethylcarboxanilido)furan

In 100 ml of benzene with stirring and cooling with ice water were dissolved 12.1 g (0.1 mole) of o-ethylaniline and 12.1 g (0.1 mole) of N,N-dimethylaniline. To this solution was added dropwise 20 ml of a benzene solution containing 15.8 g (0.1 mole) of 2,4-dimethyl-3-furoylchloride with stirring. As it is an exothermic reaction, it was kept at 20°C below the inner temperature. After the addition, the reaction mixture was heated gradually to 40°C, and it was reacted at 40°C for 1 hour. After cooling, the reaction mixture was washed successively with water, dilute hydrochloric acid, water, 5% aqueous sodium bicarbonate and water.

The product was dehydrated with anhydrous sodium sulfate. Benzene was stripped off and the solid product was recrystallized from 90% methanol to give 21.0 g of a white powdery material, melting point 108°–111°C. The yield was 86.5%.

EXAMPLE 5

Preparation of 2,4-dimethyl-3-(3-hydroxycarboxanilido)furan

To a solution of 10.9 g (0.1 mole) of 3-hydroxyaniline in 150 ml of acetone was added 8.4 g (0.1 mole) of sodium bicarbonate with cooling. To this mixture 15.9 g (0.1 mole) of 2,4-dimethyl-3-furoylchloride was added dropwise with stirring. After the addition, the reaction mixture was stirred at room temperature for 5 hours.

The reaction mixture was poured into ice water and was acidified with dilute hydrochloric acid. The precipitated crystals were filtered and washed with water, dried, and recrystallized from a mixture of methanol and water to give 21.3 g (92.0%) of white crystals, melting point 147°–148°C.

EXAMPLE 6

Preparation of 2,4-dimethyl-3-(2-ethoxycarboxanilido)furan

In 100 ml of benzene 13.7 g (0.1 mole) of 2-ethoxyaniline and 7.9 g (0.1 mole) of pyridine were dissolved with cooling with ice water. To this solution was added dropwise 20 ml of a benzene solution containing 15.8 g (0.1 mole) of 2,4-dimethyl-3-furoylchloride with stirring. The temperature was kept below 20°C during the addition. After the addition, the reaction was continued at room temperature for 2 hours. The reaction mixture was washed successively with water, dilute hydrochloric acid, water, 5% aqueous sodium bicarbonate and water. The product was dehydrated with anhydrous sodium sulfate. The benzene was stripped off and the solid product was recrystallized from 90% methanol to obtain 23.0 g of pale yellow needle-like crystals, melting point 71.5° to 73.5°C. The yield was 88.7%.

EXAMPLE 7

Preparation of 2,4-dimethyl-3-(3-methoxycarboxanilido)furan

In 100 ml of acetone with cooling with ice water were dissolved 12.3 g (0.1 mole) of m-anisidine and 8.4 g (0.1 mole) of sodium bicarbonate. To this solution was added dropwise 20 ml of an acetone solution containing 15.8 g (0.1 mole) of 2,4-dimethyl-3-furoylchloride with stirring. As it is an exothermic reaction, the temperature was kept 20°C below the inner temperature. After the addition, the reaction was continued at room temperature for 2 hours. The reaction mixture was poured into 200 ml of water and the precipitated crystals were filtered, dried and recrystallized from a mixture of benzene and n-hexane (1:2) to obtain 23.0 g of white flaky crystals, melting point 120°–123°C. The yield was 93.9%. IR cm$^{-1}$ (KBr-Tablet) $\nu_{NH}$3290(S), $\nu_{co}$1642(S), 1602(S).

EXAMPLE 8

Preparation of
2,4-dimethyl-3-(2,5-dimethoxycarboxanilido)furan

In 120 ml of benzene with stirring and cooling with ice water were dissolved 15.3 g (0.1 mole) of 2,5-dimethoxyaniline and 10.1 g (0.1 mole) of triethylamine. To this solution was added dropwise 20 ml of a benzene solution containing 15.8 g (0.1 mole) of 2,4-dimethyl-3-furoylchloride with stirring. As it is an exothermic reaction, the temperature was kept 20°C below the inner temperature. After the addition, the reaction was continued at room temperature for 2 hours. The reaction mixture was washed successively with water, dilute hydrochloric acid, water, 5% aqueous sodium bicarbonate and waer. The product was dehydrated with anhydrous sodium sulfate. The benzene was stripped off and the solid product was recrystallized from methanol to produce 22.8 g gray crystals, melting point 90°–92°C. The yield was 83.0%.

EXAMPLE 9

Preparation of
2,4-dimethyl-3-(2methoxy-5-methylcarboxanilido)furan

In 150 ml of acetone with stirring and cooling with ice water were dissolved 13.7 g (0.1 mole) of 2-methoxy-5-methylaniline and 12.1 g (0.1 mole) of N,N-dimethylaniline. To this solution was added dropwise 20 ml of an acetone solution containing 15.8 g (0.1 mole) of 2,4-dimethyl-3-furoylchloride with stirring. As it is an exothermic reaction, the temperature was kept below 20°C.

After the addition, the reaction mixture was heated gradually to 50°C. Heating was maintained at 50°C for 1 hour. After cooling, the reaction mixture was poured into 400 ml of water and the precipitated crystals were separated, dried and recrystallized from n-hexane to give 22.3 g of a pale brown mass, melting point 77.5°–78.5°C. The yield was 86.2%.

EXAMPLE 10

Preparation of
2,4-dimethyl-3-(2-chlorocarboxanilido)furan

In 100 ml of benzene with stirring and cooling with ice water were dissolved 12.8 g (0.1 01 mole) of o-chloroaniline and 10.1 g (0.1 mole) of triethylamine. To this solution was added dropwise 20 ml of a benzene solution containing 15.9 g (0.1 mole) of 2,4-dimethyl-3-furoylchloride with stirring. After the addition, the reaction was continued at room temperature for 2 hours. The reaction mixture was washed successively with water, dilute hydrochloric acid, water, 5% aqueous sodium bicarbonate and water. The benzene was stripped off and the solid product was recrystallized from methanol to obtain 21.3 g of pale yellow needle-like crystals, melting point 108°–109.5°C. The yield was 85.0%.

EXAMPLE 11

Preparation of
2,4-dimethyl-3-(3-chlorocarboxanilido)furan

To a solution of 12.8 g (0.1 mole) of m-chloroaniline in 70 ml of acetone was added 8.4 g (0.1 mole) of sodium bicarbonate. The mixture was cooled with ice water. To this mixture was added dropwise 20 ml of an acetone solution containing 15.8 g (0.1 mole) of 2,4-dimethyl-3-furoylchloride with stirring. A slight exothermic reaction resulted and carbon dioxide gas was generated. After the addition, the reaction was continued at room temperature for 2 hours. The reaction mixture was poured into 200 ml of water and the precipitated product was filtered, dried and recrystallized from a mixture of ligroine and carbon tetrachloride (4:1) to obtain 20.4 g of pale yellow powdery crystals, melting point 114°–117°C. The yield was 82.0%.

EXAMPLE 12

Preparation of
2,4-dimethyl-3-(4-bromocarboxanilido)furan

In 100 ml of benzene with stirring and cooling with ice water 17.2 g (0.1 mole) of 4-bromoaniline and 12.1 g (0.1 mole) of N,N-dimethyl aniline were dissolved. To this solution was added dropwise 20 ml of a benzene solution containing 15.8 g (0.1 mole) of 2,4-dimethyl-3-furoylchloride with stirring. After the addition, the mixture was heated gradually and the reaction was maintained at 40°C for 1 hour. After cooling, the reaction mixture was washed successively with water, dilute hydrochloricackd, 5% aqueous sodium bicarbonate and water. The benzene was stripped off and the solid product was recrystallized from methanol to obtain 24.5 g of white needle-like crystals, melting point 159°–160°C. The yield was 83.5%.

EXAMPLE 13

Preparation of
2,4-dimethyl-3-(2,4-dichlorocarboxanilido)furan

In 120 ml of ether with stirring and cooling with ice water were dissolved 16.2 g (0.1 mole) of 2,4-dichloroaniline and 7.9 g (0.1 mole) of pyridine. To this solution was added dropwise 20 ml of an ether solution containing 15.8 g (0.1 mole) 2,4-dimethyl-3-furoylchloride with stirring. As it is an exothermic reaction, the temperature was kept below 20°C. After the addition, the reaction was continued at room temperature for 2 hours. The reaction mixture was washed consecutively with water, dilute hydrochloric acid, water, 5% aqueous sodium bicarbonate and water. The ether was stripped off and the solid product was recrystallized from methanol to obtain 22.4 g of pale yellow fine needles, melting point 88.5°–90°C. The yield was 79.9%.

EXAMPLE 14

Preparation of
2,4-dimethyl-3-(2-chlorocarboxanilido)furan

To a solution of 14.1 g (0.1 mole) of 2-methyl-3-chloroaniline in 70 ml of acetone was added 8.4 g (0.1 mole) of sodium bicarbonate and the mixture was cooled with ice water. To this mixture was added dropwise 20 ml of an acetone solution containing 15.8 g (0.1 mole) of 2,4-dimethyl-3furoylchloride with stirring. A slight exothermic reaction resulted and carbon dioxide gas was generated. After the addition was complete, the reaction was continued at room temperature for 2 hours. The reaction mixture was poured into 200 ml of water and the precipitated product was filtered, washed with methanol and dried to obtain 22.7 g of powdery, white crystals, melting point 128°–132°C. The yield was 86.6%.

EXAMPLE 15

Preparation of 2,4-dimethyl-3-(3-trifluoromethylcarboxanilido)furan

In 150 ml of benzene with stirring and cooling with ice water were dissolved 16.1 g (0.1 mole) of m-trifluoromethyl aniline and 7.9 g (0.1 mole) of pyridine. To this solution was added dropwise 20 ml of benzene solution containing 15.9 g (0.1 mole) of 2,4-dimethyl-3-furoylchloride with stirring. After the addition, the reaction was continued at room temperature for 2.5 hours with stirring. The reaction mixture was washed with water to remove the pyridine hydrochloride and the product was dehydrated with anhydrous sodium sulfate. The benzene was stripped off to give 28.3 g of a brown solid product, which was recrystallized from a mixture of methanol and water to obtain 27.9 g of yellow needle-like crystals, melting point 103.5°–104.5°C. The yield was 96.0%.

EXAMPLE 16

Preparation of 2,4-dimethyl-3-(2-chloro-5-trifluoromethylcarboxonilido)furan

To a solution of 19.5 g (0.1 mole) of 2-chloro-5-trifluoromethylaniline in 100 ml of acetone was added 8.4 g (0.1 mole) of sodium bicarbonate and the mixture was cooled with ice water. To this mixture was added dropwise 30 ml of acetone solution containing 15.8 g (0.1 mole) of 2,4-dimethyl-3-furoylchloride with stirring. A slight exothermic reaction resulted and carbon dioxide gas was generated. After the addition, the reaction was continued at room temperature for 2.5 hours. The reaction mixture was poured into 500 ml of water and the precipitated product was filtered, dried and recrystallized from methanol to obtain 25.4 g of white needle-like crystals, melting point 112°–115°C. The yield was 80.2%.

EXAMPLE 17

Preparation of 2,4-dimethyl-3-(2-phenylcarboxanilido)furan

To a solution of 16.9 g (0.1 mole) of o-phenylaniline in 200 ml of benzene was added 10.1 g (0.1 mole) of triethylamine and the mixture was cooled with ice water. To this solution was added dropwise 15.9 g (0.1 mole) of 2,4-dimethyl-3-furoylchloride with stirring. After the addition, the mixture was stirred at room temperature for 3 hours. The product was washed consecutively with water, dilute hydrochloric acid and water was dehydrated with anhydrous sodium sulfate.

After the benzene was stripped off, the product was distilled under vacuum to obtain 25.8 g of a yellow viscous liquid, boiling point 167°–168°C/0.02 mmHg. The yield was 88.6%.

EXAMPLE 18

Preparation of 2,4-dimethyl-3-(carboxa-α-naphthylamido)furan

To a solution of 14.3 g (0.1 mole) of α-naphthylamine in 150 ml of acetone was added 8.4 g (0.1 mole) of sodium bicarbonate. To this misture was added dropwise 15.9 g (0.1 mole) of 2,4-dimethyl-3-furoylchloride at room temperature with stirring. The reaction product was precipitated by the addition. After the addition, the reaction mixture was stirred for 3 hours and was poured into about 80 ml of water. The precipitated product was filtered and recrystallized from methanol to obtain 24.5 g flaky white crystals, melting point 151°C. The yield was 92.3%.

EXAMPLE 19

Preparation of 2,4-dimethyl-3-(3-sodium oxycarboxanilido)furan

To 120 ml of a methanol solution containing 2.3 g (0.1 mole) of metallic sodium was added 23.1 g (0.1 mole) of 2,4-dimethyl-3-(3-hydroxycarboxanilido)furan, and the mixture was stirred at room temperature for 4 hours. The methanol was stripped off to produce 25.3 g of a pale brown powder. The product began to melt at 110°C and was completely melted at 170°C. The yield was 100%.

EXAMPLE 20

Preparation of 2,4-dimethyl-3-(3-sodium oxycarboxanilido)furan

A solution of 23.1 g (0.1 mole) 2,4-dimethyl-3-(3-hydroxycarboxanilido)furan in 200 ml of 0.5N aqueous sodium hydoxide was prepared and stored for 24 hours.

The solution was concentrated on an evaporator and was dried to obtain 25.3 g of a pale brown powder. The yield was 100%. The prouct began to melt at 120°C and was completely melted at 170°C.

EXAMPLE 21

Preparation of 2,4-dimethyl-3-(3-methoxycarboxanilido)furan

To 300 ml of anhydrous ethanol containing 3.9 g (0.1 mole) of metallic potassium was added 23.1 g (0.1 mole) of 2,4-dimethyl-3-(3-hydroxycarboxanilido)furan. The mixture was stirred at room temperature for 4 hours. To the solution was added 14.1 g (0.1 mole) of methyliodide and the mixture was stirred at 40°C for 6 hours.

After stripping off the ethanol and by-products, the residual product was dissolved in 200 ml of benzene, washed with dilute aqueous sodium hydroxide and saturated brine, and the product was dehydrated with anhydrous sodium sulfate. The benzene was stripped off and the product was recrystallized from a mixture of benzene and n-hexane (1:2) to obtain 24.2 g of flaky white crystals, melting point 120°–123°C. The yield was 99.0%.

EXAMPLE 22

Preparation of 2,4-dimethyl-3-(3-n-propoxycarboxanilido)furan

A mixture of 23.1 g (0.1 mole) of 2,4-dimethyl-3-(3-hydroxycarboxanilido)furan in 300 ml of methanol containing 2.3 g (0.1 mole) of sodium metal was stirred at a room temperature for 3 hours. To this solution was added dropwise 12.3 g (0.1 mole) of n-propylbromide. After the addition, the mixture was refluxed for 6 hours. The reaction mixture was poured into the water and the precipitated crystals were filtered, dried and recrystallized from methanol to obtain 20.4 g of pale yellow needle-like crystals, melting point 117°–228°C. The yield was 74.5%.

EXAMPLE 23

Preparation of
2,4-dimethyl-3-(3-isopropoxycarboxanilido)furan

To 200 ml of 0.5N aqueous sodium hydroxide was added 23.1 g (0.1 mole) of 2,4-dimethyl-3-(3-hydroxycarboxanilido)furan. The mixture was stirred for 2 hours, 200 ml of methanol was added to it, and 14.8 g (0.12 mole) of isopropylbromide was added dropwise with cooling with ice water. After the addition, the mixture was heated at 60°C and stirred for 4 hours. After the methanol was stripped off, the product was extracted with benzene, washed with water, and the benzene was stripped off. The product was recrystallized from a mixture of methanol and water to obtain 20.4 g of pale brown crystals, melting point 80°–82°C. The yield was 75.3%. IR cm$^{-1}$ (KBr-Tablet) $\nu_{NH}$-3320(S), $\nu_{CH}$2875(M), $\nu_{CO}$1645(S), 1602(S).

EXAMPLE 24

Preparation of
2,4-dimethyl-3-(2-ethoxy-5-methylcarboxanilido)furan

To a solution of 24.5 g (0.1 mole) of 2,4-dimethyl-3-(2-hydroxy-5-methylcarboxanilido)furan in 50 ml of 2N aqueous potassium hydroxide was added 100 ml of ethanol and 10.9 g (0.1 mole) of ethylbromide. After the addition, the mixture was heated at 50°C and stirred for 6 hours. The reaction mixture was poured into water and the precipitated crystals were separated and recrystallized from a mixture of methanol and water to obtain 23.8 g of white crystals, melting point of 79°C. The yield was 87.1%.

EXAMPLE 25

Preparation of
2,4-dimethyl-3-(3-propargyloxycarboxanilido)furan

To 250 ml of acetone were added 23.1 g (0.1 mole) of 2,4-dimethyl-3-(3-hydroxycarboxanilido)furan, 17.9 g (0.15 mole) of propargylbromide and 10.0 g (0.1 mole) of sodium carbonate. The mixture was refluxed with stirring for 8 hours. The reaction mixture was cooled and filtered. The filtrate was concentrated and the residual product was recrystallized from a mixture of methanol and water to obtain 24.9 g of white crystals, melting point 109°–111°C. The yield was 88.1 %.

EXAMPLE 26

Preparation of
2,4-dimetnyl-3-(3-allyloxycarbonoxanilido)furan

To 140 ml of anhydrous toluene were added 23.1 g (0.1 mole) of 2,4-dimethyl-3-(3-hydroxycarboxanilido)furan and 12.1 g (0.1 mole) of allybromide. The mixture was cooled and stirred and 8.0 g (0.1 mole) of pyridine was added dropwise. After the addition, the mixture was stirred at 30°C for 10 hours and the pyridine hydrobromide was separated. The product was washed with dilute aqueous sodium hydroxide, water and saturated sodium chloride, and was dehydrated with anhydrous sodium sulfate. The toluene was stripped off and the product was recrystallized from a mixture of methanol and water to obtain 19.4 g of white crystals, melting point 114°–115°C. The yield was 73.2%. IR cm$^{-1}$ (KBr Tablet) $\nu_{NH}$3280(S), $\nu_{CO}$1650(S), 1601(S).

EXAMPLE 27

Preparation of 2,4-dimethyl-3-[3-(1/2 calcium)oxycarboxanilido]furan

To a solution of 25.3 g (0.1 mole) of dimethyl-3-[3-sodium oxycarboxanilido)furan in 100 ml of ethanol was added dropwise 100 ml of an ethanol solution containing 5.5 g (0.05 mole) of calcium chloride with cooling and stirring. After the addition, the mixture was stirred at room temperature for 3 hours. The precipitated sodium chloride by-product was filtered and the ethanol was stripped off to obtain 25.0 g of a pale brown powder, which was colored at 220°C and decomposed at 250°C. The yield was 100%.

The following are typical compounds prepared by the processes of the invention. The compound number will be referred to in the following description, especially in the tests of the effects.

Compound No. 1

2,4-dimethyl-3-(2-methylcarboxanilido)furan
pink fibrile crystals
melting point 130°–132°C Compound No. 2

2,4-dimethyl-3-(3-methylcarboxanilido)furan
pale yellow crystals
melting point 117.5°–118.5°C Compound No. 3

2,4-dimethyl-3-(4-methylcarboxanilido)furan
white needle-like crystals
melting point 127.5°–128°C Compound No. 4

2,4-dimethyl-3-(2,3-dimethylcarboxanilido)furan
pale pink flaky crystals
melting point 156°–158°C Compound No. 5

2,4-dimethyl-3-(2,4-dimethylcarboxanilido)furan
pale yellow crystals
melting point 108°–112°C Compound No. 6

2,4-dimethyl-3-(2,5-dimethylcarboxanilido)furan
white powdery crystals
melting point 144°–147°C Compound No. 7

2,4-dimethyl-3-(3,4-dimethylcarboxanilido)furan
yellow flaky crystals
melting point 111°–114°C Compound No. 8

2,4-dimethyl-3-(3,5-dimethylcarboxanilido)furan
pale yellow flaky crystals
melting point 149°–152°C Compound No. 9

2,4-dimethyl-3-(2,4,6-trimethylcarboxanilido)furan
white needle-like crystals
melting point 174°–175°C Compound No. 10

2,4-dimethyl-3-(2-ethylcarboxanilido)furan
white powdery crystals melting point 108°–111°C

Compound No. 11

2,4-dimethyl-3-(2-hydroxycarboxanilido)furan
white flaky crystals
melting point 170°–171°C

Compound No. 12

2,4-dimethyl-3-(3-hydroxycarboxanilido)furan
white cyrstals
melting point 147°–148°C

Compoung No. 13

2,4-dimethyl-3-(4-hydroxycarboxanilido)furan
pale pink flaky crystals
melting point 186°–187°C

Compound No. 14

2,4-dimethyl-3-(2-methoxycarboxanilido)furan
white needle-like crystals
melting point 62°–63°C

Compound No. 15

2,4-dimethyl-3-(2-ethoxycarboxanilido)furan
pale yellow needle-like crystals
melting point 71.5°–73.5°C

Compount No. 16

2,4-dimethyl-3-(3-methoxycarboxanilido)furan
white flaky crystals
melting point 120°–123°C

Compound No. 17

2,4-dimethyl-3-(4-methoxycarboxanilido)furan
white needle-like crystals
melting point 133°–134°C

Compound No. 18

2,4-dimethyl-3-(2,5-dimethoxycarboxanilido)furan
gray crystals
melting point 90°–92°C

Compound No. 19

2,4-dimethyl-3-(2-methoxy-4-methylcarboxanilido)-furan
pale brown mass of crystals
melting point 77.5°–78.5°C

Compound No. 20

2,4-dimethyl-3-(2-ethoxy-5-methylcarboxanilido)furan
white crystals
melting point 79°C

Compound No. 21

2,4-dimethyl-3-(2-propoxy-5-methylcarboxanilido)-furan
powdery white crystals
melting point 62°–63°C

Compound No. 22

2,4-dimethyl-3-(2-n-propoxycarboxanilido)furan
white needle-like crystals
melting point 51°–53°C

Compound No. 23

2,4-dimethyl-3-(2-isopropoxycarboxanilido)furan
yellow viscous liquid
boiling point 138°–141°C/0.008 mmHg
$\eta_D^{20}$ 1.5680

Compound No. 24

2,4-dimethyl-3-(2-n-butoxycarboxanilido)furan
white needle-like crystals
melting point 68.5°–69°C

Compound No. 25

2,4-dimethyl-3-(2-allyloxycarboxanilido)furan
white feather-like crystals
melting point 59°–59.5°C

Compound No. 26

2,4-dimethyl-3-(3-n-propoxycarboxanilido)furan
pale yellow needle-like crystals
melting point 117°–118°C

Compound No. 27

2,4-dimethyl-3-(3-isopropoxycarboxanilido)furan
pale brown crystals
melting poing 80°–82°C

Compound No. 28

2,4-dimethyl-3-(3-n-butoxycarboxanilido)furan
pale brown needle-like crystals
melting point 124°–125°C

Compound No. 29

2,4-dimethyl-3-(3-n-hexyloxycarboxanilido)furan
white needle-like crystals
melting point 122°–123°C

Compound No. 30

2,4-dimethyl-3-(3-n-octyloxycarboxanilido)furan
white needle-like crystals
melting point 117°–119°C

Comound No. 31

2,5-dimethyl-3-(3-allyloxycarboxanilido)furan
white crystals
melting point114°–115°C

Compound No. 32

2,4-dimethyl-3-(3-propargyloxycarboxanilido)furan
white crystals
melting point 109°–111°C

Compound No. 33

2,4-dimethyl-3-(2-chlorocarboxanilido)furan
pale yellow needle-like crystals
melting point 108°–109.5°C

Compound No. 34

2,4-dimethyl-3-(3-chlorocarboxanilido)furan
pale yellow powdery crystals
melting point 114°–117°

Compound No. 35

2,4-dimethyl-3-(4-chlorocarboxanilido)furan
white needle-like crystals
melting point 101°–163°C

Compound No. 36

2,4-dimethyl-3-(4-bromocarboxamilido)furan
white needle-like crystals
melting point 159°–160°C

Compound No. 37

2,4-dimethyl-3-(2,4-dichlorocarboxanilido)furan
pale yellow fine needle-like crystals
melting point 88.5°–90°C

Compound No. 38

2,4-dimethyl-3-(2-methyl-3-chlorocarboxanilido)furan
white powdery crystals
melting point 128°–132°C

Compound No. 39

2,4-dimethyl-3-(2-methyl-4-chlorocarboxanilido)furan
reddish-brown powdery crystals
melting point 81.5°–85°C

Compound No. 40

2,4-dimethyl-3-(2-trifluoromethylcarboxanilido)furan
pale yellow transparent liquid
boiling point 102°–110°C/0.15 mmHg

Compoung No. 41

2,4-dimethyl-3-(3-trifluoromethylcarboxanilido)furan
yellow needle-like crystals
melting point 103.5°–104.5°C

Compound No. 42

2,4-dimethyl-3-(2-chloro-5-trifluoromethylcarboxanilido)furan
white needle-like crystals
melting point 112°–115°C

Comound No. 43

2,4-dimethyl-3-(4-cyanocarboxanilido)furan
brown needle-like crystals
melting point 140°–142°C

Compound No. 44

2,4-dimethyl-3-(4-acetylcarboxanilido)furan
pale yellow needle-like crystals
melting point 146°–147°C

Compoung No. 45

2,4-dimethyl-3-(carboxa-α-naphthylamido)furan
white flaky crystals
melting point 151°C

Compound No. 46

2,4-dimetnyl-3-(2-phenylcarboxanilido)furan
yellow viscous liquid
boiling point 167°–168°C/0.02 mmHg

Compound No. 47

2,4-dimethyl-3-(4-phenylcarboxanilido)furan
pale yellow powdery crystals
melting point 238°–242°C

Compound No. 48

2,4-dimethyl-3-(3-sodium-oxycarboxanilido)furan
pale brown powdery crystals
melting point 110°–170°C

Compound No. 49

2,4-dimethyl-3-[3-(½ calcium)-oxycarboxanolido]furan
pale brown powdery crystals
boiling point 250°C

Compound No. 50

2,4-dimethyl-3-[3-(½ copper)-oxycarbonanilido]furan
greenish blue powdery crystals
melting point above 290°C (color change at 210°C)

Compound No. 51

2,4-dimethyl-3-[3-(½ zinc)-oxycarboxanilido]furan
white powdery crystals
melting point above 290°C

Compound No. 52

2,4-dimethyl-3-[3-(⅛ iron)-ocycarboxanilido]furan
white powdery crystals
melting point 147°C

Compound No. 53

2,4-dimethyl-3-[3-(¼ tin)-oxycarboxanilido]furan
white powdery crystals
melting point above 290°C

Compound No. 54

2,4-dimethyl-3-[3-(½ magnesium)-oxycarboxanilido]furan
brown powdery crystals
melting point above 290°C Certain examples of preparations of compositions of the compounds of the invention and the tests for inhibiting diseases of agricultural plants by applying them will now be illustrated.

The active ingredient can be used in the form of conventional compositions, e.g. solution, emulsion, wettable powder, fine granules, granules and powder. Moreover, it is possible to apply the active ingredient above without any other additive. These compositions can be prepared by the conventional method of mixing the active ingredient with an extending agent such as a liquid or solid diluent carrier, or, if necessary, with an emulsifier or a dispersing agent.

Suitable liquid diluents or carriers include water, aromatic hydrocarbons, e.g., xylene, benzene and methyl naphthalene; chlorinated aromatic hydrocarbons, e.g., chlorobenzene; mineral oil, e.g. paraffin; alcohols, e.g. methanol, propanol; a polar solvent, e.g. dimethylformamide, dimethylsulfoxide, etc.

The solid diluent or carrier can be talc, clay, caoline, hydrated silica, wood powder, sand, etc. The emulsifier can be a polyoxyethylene ester of an aliphatic carboxylic acid, a polyoxyethylene ether of an aliphatic alcohol, etc.

The dispersing agent can be alkali metal salts, alkaline earth metal salts or ammonium salts of an alkyl sulfonic acid, alkylarylsulfonic acid or lignin sulfonic acid or methylcellulose, etc.

The active ingredient can be combined with other germicidal compounds, e.g. Neo Asozin (ferric ammonium salts of methane arsonic acid), Polyoxin (antibiotic fungicide), Validamycin (antibiotic fungicide), phenazine (phenazine-5-oxide); insecticidal compounds, e.g. Sumithion [O,O-dimethyl O-(3-methyl-4- nitrophenyl) phosphorothioate], Baycid (O,O-dimethyl 0-[3-methyl-4-methylthiophenyl)phosphorothioate], Spanon [N'-(2-methyl-4-chlorophenyl)-N,N-dimethylformamidine]; miticides, nematocides, etc. to impart a synergistic effect.

It is also possible to combine the composition of this invention with a fertilizer, soil improver, etc. Certain examples of formulations of compositions where the active ingredient is a compound of the invention are provided for purposes of illustration only and are not intended to limit the invention.

[Composition No. 1]Powder

4% of Compound No. 1, 5% diatomaceous earth and 1% clay were crushed and uniformly mixed to yield a powdery composition.

[Composition No. 2]Wettable Powder

50% of Compound No. 2, 45% diatomaceous earch, 2% sodium dinaphthylmethane sulfonate and 3% sodium lignine sulfonate were mixed and crushed uniformly to yield a wettable powder.

[Composition No. 3]Emulsion

30% Compound No. 3, 20% cyclohexanone, 11% polyoxyethylene alkylaryl ether, 4% calcium alkylbenzene sulfonate and 35% methyl naphthalene were uniformly mixed to yield an emulsion.

[Composition No. 4]Fine granules

4% polyethyleneglycol was added to sea sand (60–250 mesh) and the mixture was vigorously stirred to coat the polyethyleneglycol uniformly on the surface of the sea sand. To 94% of the mixture was added 6% of a mixture consisting of 70% Compound 5 and 30% clay, and the mixture was vigorously stirred to yield granules. [Composition No. 5]Granules 5% Compound No. 5, 2% sodium lauryl sulfate, 5% sodium lignine sulfonate, 2% carboxymethyl cellulose and 86% clay were uniformly mixed and crushed. One part of water was added to 5 parts of the mixture and kneaded and extruded through the screen of an extrusion granulating machine. The extruded composition was then dried and sifted using 14 –32 mesh sieve.

The application of the composition is illustrated as follows:

When the resulting composition is used as an agricultural germicide, a dilute solution containing 50–2000 ppm of the active ingredient is sprayed at a rate of 50–300 l per 10 a on up-land. The powder containing 0.1–20% of the active ingredient is sprayed at a rate of 1–5 kg per 10 a. In soil, it is applied at a rate of 100–5000 kg of the active ingredient per 10 a. If a disease is to be prevented by applying to seeds, the seeds are immersed in a solution containing 500–100,000 ppm for 1–100 hours or they are coated with a powder containing 0.01–20% of the active ingredient.

The effects of the germicidal agents for agricultural purposes of the invention are shown by certain experiments.

EXPERIMENT 1

Rice sheath blight inhibition test

A porcelain pot having a diameter of 9 cm was filled with paddy soil and was filled with water so as to be in a wet condition. Fifteen rice seedlings (Kinmaze Type) were transplanted. When the seedlings had grown to show 6 leaves, a germicidal solution was prepared by dissolving wettable powders prepared as in "Composition No. 2" in water and 50 ml of the solution was applied to each pot.

After drying the pot, sheath blight bacteria (*Pellecularia sukaki*) cultures on a flat potato culture medium (circular culture having a diameter of 9 mm) was inoculated into the sheath of the seedlings. The pot was kept in a green house. After 8 days, the length of the leaf spot of sheath blight formed on the sheaths was measured. The results of the tests (3 pots were used for each test) are shown in Table 1.

The inhibition rate was calculated as follows:

$$\text{Inhibition rate (\%)} = \left(1 - \frac{\text{total length of lesion in treated zone}}{\text{total length of lesion in non-treated zone}}\right) \times 100$$

Table 1

| Germicidal ingredient | | Concentration (ppm) | Total length of lesion (cm) | Inhibition rate (%) | (Chemical injury) Phytotoxicity |
|---|---|---|---|---|---|
| Compound | No. 1 | 500 | 12 | 97.3 | None |
| | No. 2 | " | 0 | 100 | " |
| | No. 3 | " | 36 | 91.8 | " |
| | No. 4 | " | 7 | 98.4 | " |
| | No. 5 | " | 29 | 93.4 | " |
| | No. 6 | " | 4 | 99.1 | " |
| | No. 7 | " | 31 | 93.0 | " |
| | No. 8 | " | 0 | 100 | " |
| | No. 9 | " | 52 | 88.2 | " |
| | No. 10 | " | 14 | 96.8 | " |
| | No. 11 | " | 29 | 93.4 | " |
| | No. 12 | " | 12 | 97.3 | " |
| | No. 13 | " | 52 | 88.2 | " |
| | No. 14 | " | 16 | 96.4 | " |
| | No. 15 | " | 24 | 94.6 | " |
| | No. 16 | " | 0 | 100 | " |
| | No. 17 | " | 49 | 88.9 | " |
| | No. 18 | " | 11 | 97.5 | " |
| | No. 19 | " | 8 | 98.2 | " |
| | No. 20 | " | 12 | 97.3 | " |
| | No. 21 | " | 14 | 96.8 | " |
| | No. 22 | " | 48 | 89.1 | " |
| | No. 23 | " | 26 | 94.1 | " |
| | No. 24 | " | 31 | 92.9 | " |

Table 1-continued

| Germicidal ingredient | Concentration (ppm) | Total length of lesion (cm) | Inhibition rate (%) | (Chemical injury) Phytotoxicity |
|---|---|---|---|---|
| No. 25 | '' | 18 | 95.9 | '' |
| No. 26 | '' | 2 | 99.5 | '' |
| No. 27 | '' | 1 | 99.8 | '' |
| No. 28 | '' | 0 | 100 | '' |
| No. 29 | '' | 0 | 100 | '' |
| No. 30 | '' | 14 | 96.8 | '' |
| No. 31 | '' | 4 | 99.3 | '' |
| No. 32 | '' | 3 | 99.3 | '' |
| No. 33 | '' | 15 | 96.6 | '' |
| No. 34 | '' | 2 | 99.5 | '' |
| No. 35 | '' | 24 | 94.6 | '' |
| No. 36 | '' | 8 | 98.2 | '' |
| No. 37 | '' | 32 | 92.7 | '' |
| No. 38 | '' | 6 | 98.6 | '' |
| No. 39 | '' | 27 | 93.9 | '' |
| No. 40 | '' | 24 | 94.6 | '' |
| No. 41 | '' | 0 | 100 | '' |
| No. 42 | '' | 15 | 96.6 | '' |
| No. 43 | '' | 48 | 89.1 | '' |
| No. 44 | '' | 52 | 88.2 | '' |
| No. 45 | '' | 46 | 89.6 | '' |
| No. 46 | '' | 32 | 92.7 | '' |
| No. 47 | '' | 49 | 88.9 | '' |
| No. 48 | '' | 11 | 97.5 | '' |
| No. 49 | '' | 0 | 100 | '' |
| No. 50 | '' | 2 | 99.5 | '' |
| No. 51 | '' | 0 | 100 | '' |
| No. 52 | '' | 4 | 99.3 | '' |
| No. 53 | '' | 8 | 98.2 | '' |
| No. 54 | '' | 6 | 98.6 | '' |

The compounds disclosed in German Pat. Application Publication No. 2,006,471 and No. 2,006,472

Reference compound No. 101

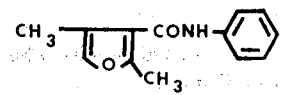

| | 500 | 426 | 3.4 | None |

Reference compound No. 102

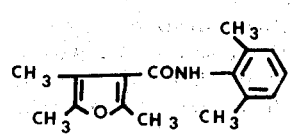

| | '' | 394 | 10.7 | '' |

Reference compound No. 103

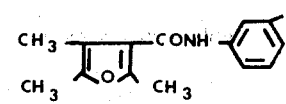

| | '' | 296 | 31.9 | '' |

Reference compound No. 104

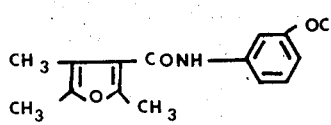

| | '' | 301 | 31.8 | '' |

Reference compound No. 105

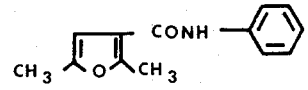

| | '' | 361 | 18.1 | '' |

Reference compound No. 106

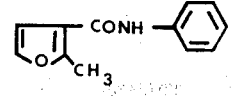

| | '' | 430 | 2.5 | '' |

Reference compound No. 107

Table 1-continued

| Germicidal ingredient | Concentration (ppm) | Total length of lesion (cm) | Inhibition rate (%) | (Chemical injury) Phytotoxicity |
|---|---|---|---|---|
| 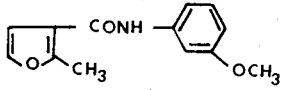 | " | 319 | 27.7 | " |
| Reference compound No. 108 | | | | |
| 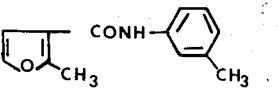 | " | 308 | 30.2 | " |
| Reference compound No. 109 | | | | |
| Vitavax (2,3-dihydro-5-carboxanilido-6-methyl-1,4-oxathiin) | " | 142 | 67.8 | " |
| Reference compound No. 110 | | | | |
| Plantvax (2,3-dihydro-5-carboxanilido-6-methyl-1,4-oxathiin-4,4-dioxide) | " | 124 | 71.9 | " |
| Reference compound No. 111 | | | | |
| Polyoxine PS emulsion (antibiotic fungicide polyoxine B 3% (30,000 p.m.u./g) | 25 | 52 | 88.2 | " |
| Reference compound No. 112 | | | | |
| Neo Asozin solution (ferric ammonium salts of methane arsonic acid 6.5%) | 16.2 | 0 | 100 | " |
| Non-treated pot | — | 441 | 0 | " |

EXPERIMENT 2

Haricot Stem Rot Inhibition Test

Haricot seedlings at the two leaf stage (Edogawa type haricot seedings) were each planted in porcelain pots having diameters of 15 cm. Each germicidal solution was prepared by dissolving wettable powders prepared as "Composition No. 2" with water. 15 ml of the solution was sprayed to each pot. Haricot stem rot cultures in an agar medium containing potato soup (diameter 6 mm) was inoculated into each seedling after 1 day. After 4 days, each infected condition was observed under the following evaluation standard levels. The results of the tests are shown in Table 2.

$n_0$ : number of leaves which are not infected;
$n_1$ : number of leaves which are infected at or around only the inoculated part;
$n_2$ : number of leaves which are about 1/5 infected;
$n_3$ : number of leaves which are about 2/5 infected;
$n_4$ : number of leaves which are about 3/5 infected;
$n_5$ : number of leaves which are about 4/5 infected;

$$\text{Degree of infection} = \frac{(0 \times n_0) + (1 \times n_1) = \ldots (5 \times n_5)}{5(n_0+n_1+n_2+n_4+n_5)}$$

wherein $n$ represents the total number of leaves measured.

TABLE 2

| Germicidal ingredient | | Concentration (ppm) | Degree of infection (%) | (Chemical injury) Phytotoxicity |
|---|---|---|---|---|
| Compound | No. 1 | 500 | 1.2 | None |
| | No. 2 | " | 0.0 | " |
| | No. 3 | " | 1.4 | " |
| | No. 4 | " | 0.7 | " |
| | No. 5 | " | 0.8 | " |
| | No. 6 | " | 0.4 | " |
| | No. 7 | " | 1.5 | " |
| | No. 8 | " | 0.0 | " |
| | No. 9 | " | 2.1 | " |
| | No. 10 | " | 0.4 | " |
| | No. 11 | " | 2.4 | " |
| | No. 12 | " | 0.2 | " |
| | No. 13 | " | 2.1 | " |
| | No. 14 | " | 1.4 | " |
| | No. 15 | " | 0.8 | " |
| | No. 16 | " | 0.0 | " |
| | No. 17 | " | 2.4 | " |
| | No. 18 | " | 1.3 | " |
| | No. 19 | " | 0.7 | " |
| | No. 20 | " | 1.3 | " |
| | No. 21 | " | 1.2 | " |
| | No. 22 | " | 1.3 | " |
| | No. 23 | " | 1.0 | " |
| | No. 24 | " | 0.3 | " |

TABLE 2-continued

| Germicidal ingredient | Concentration (ppm) | Degree of infection (%) | (Chemical injury) Phytotoxicity |
|---|---|---|---|
| No. 25 | '' | 1.1 | '' |
| No. 26 | '' | 0.2 | '' |
| No. 27 | '' | 0.0 | '' |
| No. 28 | '' | 0.0 | '' |
| No. 29 | '' | 0.0 | '' |
| No. 30 | '' | 0.8 | '' |
| No. 31 | '' | 0.2 | '' |
| No. 32 | '' | 0.0 | '' |
| No. 33 | '' | 1.3 | '' |
| No. 34 | '' | 0.7 | '' |
| No. 35 | '' | 0.4 | '' |
| No. 36 | '' | 0.3 | '' |
| No. 37 | '' | 1.6 | '' |
| No. 38 | '' | 1.0 | '' |
| No. 39 | '' | 2.0 | '' |
| No. 40 | '' | 1.4 | '' |
| No. 41 | '' | 0.3 | '' |
| No. 42 | '' | 0.7 | '' |
| No. 43 | '' | 0.9 | '' |
| No. 44 | '' | 1.2 | '' |
| No. 45 | '' | 2.4 | '' |
| No. 46 | '' | 1.3 | '' |
| No. 47 | '' | 2.1 | '' |
| No. 48 | '' | 1.2 | '' |
| No. 49 | '' | 0.7 | '' |
| No. 50 | '' | 0.3 | '' |
| No. 51 | '' | 0.9 | '' |
| No. 52 | '' | 0.6 | '' |
| No. 53 | '' | 1.0 | '' |
| No. 54 | '' | 1.2 | '' |

The compounds disclosed in German Pat. Application Publication No. 2,006,471 and No. 2,006,472

Reference compound No. 101

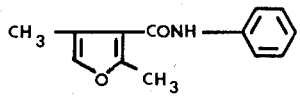

| | 500 | 4.2 | None |

Reference compound No. 107

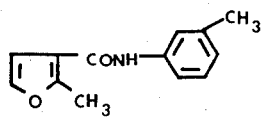

| | '' | 4.0 | '' |

| Non-treated pot | — | 4.7 | '' |

EXPERIMENT 3

Cucumber Fusarium wilt Inhibition Test

A wheat bran medium containing cucumber Fusarium wilt bacteria was mixed in a 1:20 ratio with soil sterilized in an autoclave to prepare the inoculated soil. Each porcelain pot, 9 cm in diameter was filled with 100 G of sterilized soil. The soil inoculated with Fusarium wilt was mixed with wettable powders prepared as in "Composition No. 2" and 100 g of the soil mixture was placed in the porcelain pots.

10 Cucumber weeds were sown in the pots on the next day. A germination rate and normally grown seedlings rate were measured after 3 days. Three pots were used for one text.

$$\text{Germination rage} = \frac{\text{number of germinated seeds}}{\text{total number of seeds}} \times 100$$

$$\text{Normally grown seedling rate} = \frac{\text{number of normally grown seedlings}}{\text{number of total seedlings}} \times 100$$

Table 3

| Germicidal ingredient | | Dose (kg/100) | Germination rate (%) | normally grown seedling rate (%) |
|---|---|---|---|---|
| Compound | No.1 | 1.0 | 93.3 | 100 |
| | No.2 | '' | 100 | 100 |
| | No.3 | '' | 100 | 90.0 |
| | No.4 | '' | 100 | 100 |
| | No.5 | '' | 96.7 | 93.1 |
| | No.6 | '' | 100 | 100 |
| | No.7 | '' | 90.0 | 96.3 |
| | No.8 | '' | 100 | 100 |

Table 3-continued

| Germicidal ingredient | Dose (kg/100) | Germination rate (%) | normally grown seedling rate (%) |
|---|---|---|---|
| No.9 | " | 100 | 93.3 |
| No.10 | " | 100 | 100 |
| No.11 | " | 96.7 | 93.1 |
| No.12 | " | 100 | 100 |
| No.13 | " | 100 | 93.3 |
| No.14 | " | 100 | 100 |
| No.15 | " | 100 | 100 |
| No.16 | " | 100 | 100 |
| No.17 | " | 96.7 | 93.1 |
| No.18 | " | 96.7 | 100 |
| No.19 | " | 100 | 100 |
| No.20 | " | 100 | 100 |
| No.21 | " | 100 | 100 |
| No.22 | " | 100 | 90.0 |
| No.23 | " | 100 | 100 |
| No.24 | " | 100 | 100 |
| No.25 | " | 100 | 93.3 |
| No.26 | " | 100 | 100 |
| No.27 | " | 100 | 100 |
| No.28 | " | 100 | 100 |
| No.29 | " | 100 | 100 |
| No.30 | " | 100 | 100 |
| No.31 | " | 100 | 100 |
| No.32 | " | 100 | 100 |
| No.33 | " | 90.0 | 100 |
| No.34 | " | 100 | 100 |
| No.35 | " | 100 | 100 |
| No.36 | " | 100 | 100 |
| No.37 | " | 100 | 93.3 |
| No.38 | " | 100 | 90.0 |
| No.39 | " | 96.7 | 93.1 |
| No.40 | " | 96.7 | 100 |
| No.41 | " | 100 | 100 |
| No.42 | " | 100 | 93.3 |
| No.43 | " | 96.7 | 93.1 |
| No.44 | " | 100 | 93.3 |
| No.45 | " | 96.7 | 96.2 |
| No.46 | " | 100 | 100 |
| No.47 | " | 100 | 93.3 |
| No.48 | " | 100 | 90.0 |
| No.49 | " | 100 | 100 |
| No.50 | " | 100 | 100 |
| No.51 | " | 100 | 100 |
| No.52 | " | 100 | 100 |
| No.53 | " | 100 | 100 |
| No.54 | " | 100 | 100 |

The compounds disclosed in German Pat. Application Publication No. 2,006,471 and No. 2,006,472

Reference compound No. 101

| | 1.0 | 86.7 | 38.5 |

Reference compound No. 107

| | 1.0 | 66.7 | 50.5 |

| Ground emulsion (mixture of 2,3-dibromo-propionitrile 20%) and 1,1,1-trichloro-2-nitro-ethylene 20%) 1000 times dilute solution | | 83.3 | 80.0 |
| 3000 l treatment Bacterial inoculated soil pot | | 70.0 | 4.6 |
| Sterilized soil pot | | 100 | 100 |

EXPERIMENT 4

Cucumber Rhizoctonia Solani Inhibition Test

Each porcelain pot, 9 cm in diameter was filled with sand and 10 cucumber seeds (Sagami Hanzero Type) were sown. Each wettable powder prepared as in "Composition No. 2" was diluted to 500, 250 or 125 ppm of the active ingredient and 30 ml of the dilute solution was placed in each pot.

Rhizoctonia Solani cultures on wheat bran culture was diluted 10 times with soil after 2 days. 10 g of the Rhizoctonia Solani-containing soil was placed in each pot. After the inoculation, the pot was kept in a plant room at 25°C in a specific humidity (90%) for 2 days and 6 days. The number of normally grown seedlings was counted. Three pots were used for one test.

$$\text{Normally grown seedling rate} = \frac{\text{number of normally grown seedlings}}{\text{number of total seedlings}} \times 100$$

The results are shown in Table 4.

Table 4

| Germicidal ingredient | | Concentration (ppm) | Normally grown seedling rate (%) | | (Chemical injury) Phytotoxicity |
|---|---|---|---|---|---|
| | | | After 2 days | After 6 days | |
| Compound | No. 1 | 500 | 100 | 100 | None |
| | | 250 | 100 | 93.3 | '' |
| | | 125 | 100 | 90.0 | '' |
| | No. 2 | 500 | 100 | 100 | '' |
| | | 250 | 100 | 100 | '' |
| | | 125 | 100 | 100 | '' |
| | No. 3 | 500 | 100 | 100 | '' |
| | | 250 | 100 | 90.0 | '' |
| | | 125 | 96.7 | 83.3 | '' |
| | No.4 | 500 | 100 | 100 | '' |
| | | 250 | 100 | 100 | '' |
| | | 125 | 100 | 93.3 | '' |
| | No.5 | 500 | 100 | 100 | '' |
| | | 250 | 100 | 90.0 | '' |
| | | 125 | 96.7 | 80.0 | '' |
| | No.6 | 500 | 100 | 100 | '' |
| | | 250 | 100 | 100 | '' |
| | | 125 | 100 | 93.3 | '' |
| | No.7 | 500 | 100 | 100 | '' |
| | | 250 | 100 | 100 | '' |
| | | 125 | 100 | 100 | '' |
| | No.8 | 500 | 100 | 100 | '' |
| | | 250 | 100 | 100 | '' |
| | | 125 | 100 | 100 | '' |
| | No.9 | 500 | 100 | 100 | '' |
| | | 250 | 100 | 93.3 | '' |
| | | 125 | 96.7 | 80.0 | '' |
| | No.10 | 500 | 100 | 100 | '' |
| | | 250 | 100 | 100 | '' |
| | | 125 | 100 | 100 | '' |
| | No.11 | 500 | 100 | 100 | '' |
| | | 250 | 100 | 93.3 | '' |
| | | 125 | 100 | 80.0 | '' |
| | No.12 | 500 | 100 | 100 | '' |
| | | 250 | 100 | 100 | '' |
| | | 125 | 100 | 100 | '' |
| | No.13 | 500 | 100 | 100 | '' |
| | | 250 | 100 | 90.0 | '' |
| | | 125 | 100 | 86.7 | '' |
| | No.14 | 500 | 100 | 100 | '' |
| | | 250 | 100 | 100 | '' |
| | | 125 | 100 | 93.3 | '' |
| | No.15 | 500 | 100 | 100 | '' |
| | | 250 | 100 | 100 | '' |
| | | 125 | 100 | 100 | '' |
| | No.16 | 500 | 100 | 100 | '' |
| | | 250 | 100 | 100 | '' |
| | | 125 | 100 | 100 | '' |
| | No.17 | 500 | 100 | 100 | '' |
| | | 250 | 100 | 100 | '' |
| | | 125 | 100 | 90.0 | '' |
| | No.18 | 500 | 100 | 100 | '' |
| | | 250 | 100 | 100 | '' |
| | | 125 | 100 | 100 | '' |
| | No.19 | 500 | 100 | 100 | '' |
| | | 250 | 100 | 100 | '' |
| | | 125 | 100 | 100 | '' |
| | No.20 | 500 | 100 | 100 | '' |
| | | 250 | 100 | 100 | '' |
| | | 125 | 100 | 90.0 | '' |
| | No.21 | 500 | 100 | 100 | '' |
| | | 250 | 100 | 100 | '' |
| | | 125 | 100 | 100 | '' |
| | No.22 | 500 | 100 | 100 | '' |
| | | 250 | 100 | 100 | '' |
| | | 125 | 100 | 86.7 | '' |
| | No.23 | 500 | 100 | 100 | '' |
| | | 250 | 100 | 100 | '' |
| | | 125 | 100 | 90.0 | '' |
| | No.24 | 500 | 100 | 100 | '' |
| | | 250 | 100 | 93.3 | '' |
| | | 125 | 100 | 80.0 | '' |
| | No.25 | 500 | 100 | 100 | '' |
| | | 250 | 100 | 100 | '' |
| | | 125 | 100 | 100 | '' |
| | No.26 | 500 | 100 | 100 | '' |
| | | 250 | 100 | 100 | '' |
| | | 125 | 100 | 100 | '' |
| | No.27 | 500 | 100 | 100 | '' |

Table 4-continued

| Germicidal ingredient | Concentration (ppm) | Normally grown seedling rate (%) After 2 days | Normally grown seedling rate (%) After 6 days | (Chemical injury) Phytotoxicity |
|---|---|---|---|---|
| No.28 | 250 | 100 | 100 | '' |
|  | 125 | 100 | 100 | '' |
| No.29 | 500 | 100 | 100 | '' |
|  | 250 | 100 | 100 | '' |
|  | 125 | 100 | 100 | '' |
| No.30 | 500 | 100 | 100 | '' |
|  | 250 | 100 | 100 | '' |
|  | 125 | 100 | 100 | '' |
| No.31 | 500 | 100 | 100 | '' |
|  | 250 | 100 | 100 | '' |
|  | 125 | 100 | 100 | '' |
| No.32 | 500 | 100 | 100 | '' |
|  | 250 | 100 | 100 | '' |
|  | 125 | 100 | 100 | '' |
| No.33 | 500 | 100 | 100 | '' |
|  | 250 | 100 | 93.3 | '' |
|  | 125 | 100 | 80.0 | '' |
| No.34 | 500 | 100 | 100 | '' |
|  | 250 | 100 | 100 | '' |
|  | 125 | 100 | 100 | '' |
| No.35 | 500 | 100 | 100 | '' |
|  | 250 | 100 | 90.0 | '' |
|  | 125 | 100 | 76.7 | '' |
| No.36 | 500 | 100 | 100 | '' |
|  | 250 | 100 | 100 | '' |
|  | 125 | 100 | 93.3 | '' |
| No.37 | 500 | 100 | 100 | '' |
|  | 250 | 100 | 90.0 | '' |
|  | 125 | 100 | 96.7 | '' |
| No.38 | 500 | 100 | 100 | '' |
|  | 250 | 100 | 100 | '' |
|  | 125 | 100 | 96.7 | '' |
| No.39 | 500 | 100 | 100 | '' |
|  | 250 | 100 | 90.0 | '' |
|  | 125 | 100 | 70.0 | '' |
| No.40 | 500 | 100 | 100 | '' |
|  | 250 | 100 | 93.3 | '' |
|  | 125 | 100 | 90.0 | '' |
| No.41 | 500 | 100 | 100 | '' |
|  | 250 | 100 | 100 | '' |
|  | 125 | 100 | 100 | '' |
| No.42 | 500 | 100 | 100 | '' |
|  | 250 | 100 | 100 | '' |
|  | 125 | 100 | 93.3 | '' |
| No.43 | 500 | 100 | 100 | '' |
|  | 250 | 100 | 93.3 | '' |
|  | 125 | 100 | 90.0 | '' |
| No.44 | 500 | 100 | 100 | '' |
|  | 250 | 100 | 90.0 | '' |
|  | 125 | 100 | 76.7 | '' |
| No.45 | 500 | 100 | 100 | '' |
|  | 250 | 100 | 100 | '' |
|  | 125 | 100 | 90.0 | '' |
| No.46 | 500 | 100 | 100 | '' |
|  | 250 | 100 | 100 | '' |
|  | 125 | 100 | 100 | '' |
| No.47 | 500 | 100 | 100 | '' |
|  | 250 | 100 | 93.3 | '' |
|  | 125 | 100 | 86.7 | '' |
| No.48 | 500 | 100 | 100 | '' |
|  | 250 | 100 | 93.3 | '' |
|  | 125 | 100 | 83.3 | '' |
| No.49 | 500 | 100 | 100 | '' |
|  | 250 | 100 | 100 | '' |
|  | 125 | 100 | 100 | '' |
| No.50 | 500 | 100 | 100 | '' |
|  | 250 | 100 | 100 | '' |
|  | 125 | 100 | 100 | '' |
| No.51 | 500 | 100 | 100 | None |
|  | 250 | 100 | 100 | '' |
|  | 125 | 100 | 100 | '' |
| No.52 | 500 | 100 | 100 | '' |
|  | 250 | 100 | 100 | '' |
|  | 125 | 100 | 100 | '' |
| Benlate wettable powder (methyl-1-(butylcarbamoyl)-2-benzimidazole carbamate 50%) | 500 | 100 | 53.3 | None |
|  | 250 | 90.0 | 36.7 | '' |
|  | 125 | 83.3 | 13.3 | '' |
| Captan wettable powder N-trichloromethyl thio-4-cyclohexane-1,2-dicarboximide (50%) | 500 | 100 | 10.0 | Slight injury |
|  | 250 | 86.7 | 3.3 | Very slightly injured |
|  | 125 | 60.0 | 0.0 | None |

Table 4-continued

| Germicidal ingredient | Concentration (ppm) | Normally grown seedling rate (%) | | (Chemical injury) Phytotoxicity |
|---|---|---|---|---|
| | | After 2 days | After 6 days | |
| Non-treated pot | — | 0.0 | 0.0 | '' |

EXPERIMENT 5

Cotton seedling blight inhibition test

Each wettable powder prepared as in "Composition No. 2" was applied to cotton seeds at a rate of 1.0, 0.5 of 0.1% of the weight of the cotton seeds. *Rhizoctonia Solani* cultured on wheat bran culture was diluted 40 times with soil. The *Rhizoctonia Solani*-containing soil was placed in each pot, of 15 cm diameter, and 20 treated cotton seeds were placed in the soil.

The pot was kept in a green house until the two-leaf stage and then it was kept in a plant room at 25°C. A specific humidity (90%) for 2 days. The number of normally grown seedlings was counted. Two pots were used for one test.

$$\text{Normally grown seedling rate (\%)} = \frac{\text{number of normally grown seedlings}}{\text{number of total seedlings}} \times 100$$

Table 5

| Germicidal ingredient | | Concentration (%) | Normally grown seedling rate (%) | (Chemical injury) Phytotoxicity |
|---|---|---|---|---|
| Compound | No.1 | 1.0 | 100 | None |
| | | 0.5 | 100 | '' |
| | | 0.1 | 95.0 | '' |
| | No.2 | 1.0 | 100 | '' |
| | | 0.5 | 100 | '' |
| | | 0.1 | 100 | '' |
| | No.3 | 1.0 | 100 | '' |
| | | 0.5 | 97.5 | '' |
| | | 0.1 | 90.0 | '' |
| | No.4 | 1.0 | 100 | '' |
| | | 0.5 | 100 | '' |
| | | 0.1 | 100 | '' |
| | No.5 | 1.0 | 100 | '' |
| | | 0.5 | 100 | '' |
| | | 0.1 | 95.0 | '' |
| | No.6 | 1.0 | 100 | '' |
| | | 0.5 | 100 | '' |
| | | 0.1 | 100 | '' |
| | No.7 | 1.0 | 100 | '' |
| | | 0.5 | 100 | '' |
| | | 0.1 | 92.5 | '' |
| | No.8 | 1.0 | 100 | '' |
| | | 0.5 | 100 | '' |
| | | 0.1 | 100 | '' |
| | No.9 | 1.0 | 100 | '' |
| | | 0.5 | 95.0 | '' |
| | | 0.1 | 87.5 | '' |
| | No.10 | 1.0 | 100 | '' |
| | | 0.5 | 100 | '' |
| | | 0.1 | 100 | '' |
| | No.11 | 1.0 | 100 | '' |
| | | 0.5 | 100 | '' |
| | | 0.1 | 97.5 | '' |
| | No.12 | 1.0 | 100 | '' |
| | | 0.5 | 100 | '' |
| | | 0.1 | 100 | '' |
| | No.13 | 1.0 | 100 | '' |
| | | 0.5 | 97.5 | '' |
| | | 0.1 | 95.0 | '' |
| | No.14 | 1.0 | 100 | '' |
| | | 0.5 | 100 | '' |
| | | 0.1 | 97.5 | '' |
| | No.15 | 1.0 | 100 | '' |
| | | 0.5 | 100 | '' |
| | | 0.1 | 100 | '' |
| | No.16 | 1.0 | 100 | '' |
| | | 0.5 | 100 | '' |
| | | 0.1 | 100 | '' |
| | No.17 | 1.0 | 100 | '' |
| | | 0.5 | 100 | '' |
| | | 0.1 | 95.0 | '' |
| | No.18 | 1.0 | 100 | '' |
| | | 0.5 | 100 | '' |
| | | 0.1 | 95.0 | '' |
| | No.19 | 1.0 | 100 | '' |
| | | 0.5 | 100 | '' |
| | | 0.1 | 92.5 | '' |
| | No.20 | 1.0 | 100 | '' |
| | | 0.5 | 100 | '' |
| | | 0.1 | 100 | '' |
| | No.21 | 1.0 | 100 | '' |

Table 5-continued

| Germicidal ingredient | Concentration (%) | Normally grown seedling rate (%) | (Chemical injury) Phytotoxicity |
|---|---|---|---|
| | 0.5 | 100 | ″ |
| | 0.1 | 100 | ″ |
| No.22 | 1.0 | 100 | ″ |
| | 0.5 | 100 | ″ |
| | 0.1 | 97.5 | ″ |
| No.23 | 1.0 | 100 | ″ |
| | 0.5 | 100 | ″ |
| | 0.1 | 100 | ″ |
| No.24 | 1.0 | 100 | ″ |
| | 0.5 | 100 | ″ |
| | 0.1 | 100 | ″ |
| No.25 | 1.0 | 100 | ″ |
| | 0.5 | 100 | ″ |
| | 0.1 | 90.0 | ″ |
| No.26 | 1.0 | 100 | ″ |
| | 0.5 | 100 | ″ |
| | 0.1 | 100 | ″ |
| No.27 | 1.0 | 100 | ″ |
| | 0.5 | 100 | ″ |
| | 0.1 | 100 | ″ |
| No.28 | 1.0 | 100 | ″ |
| | 0.5 | 100 | ″ |
| | 0.1 | 100 | ″ |
| No.29 | 1.0 | 100 | ″ |
| | 0.5 | 100 | ″ |
| | 0.1 | 100 | ″ |
| No.30 | 1.0 | 100 | ″ |
| | 0.5 | 100 | ″ |
| | 0.1 | 100 | ″ |
| No.31 | 1.0 | 100 | ″ |
| | 0.5 | 100 | ″ |
| | 0.1 | 100 | ″ |
| No.32 | 1.0 | 100 | ″ |
| | 0.5 | 100 | ″ |
| | 0.1 | 100 | ″ |
| No.33 | 1.0 | 100 | ″ |
| | 0.5 | 100 | ″ |
| | 0.1 | 95.0 | ″ |
| No.34 | 1.0 | 100 | ″ |
| | 0.5 | 100 | ″ |
| | 0.1 | 100 | ″ |
| No.35 | 1.0 | 100 | ″ |
| | 0.5 | 97.5 | ″ |
| | 0.1 | 92.5 | ″ |
| No.36 | 1.0 | 100 | ″ |
| | 0.5 | 100 | ″ |
| | 0.1 | 97.5 | ″ |
| No.37 | 1.0 | 100 | ″ |
| | 0.5 | 95.0 | ″ |
| | 0.1 | 85.0 | ″ |
| No.38 | 1.0 | 100 | ″ |
| | 0.5 | 100 | ″ |
| | 0.1 | 97.5 | ″ |
| No.39 | 1.0 | 100 | ″ |
| | 0.5 | 92.5 | ″ |
| | 0.1 | 80.0 | ″ |
| No.40 | 1.0 | 100 | ″ |
| | 0.5 | 97.5 | ″ |
| | 0.1 | 92.5 | ″ |
| No.41 | 1.0 | 100 | ″ |
| | 0.5 | 100 | ″ |
| | 0.1 | 100 | ″ |
| No.42 | 1.0 | 100 | ″ |
| | 0.5 | 100 | ″ |
| | 0.1 | 97.5 | ″ |
| No.43 | 1.0 | 97.5 | ″ |
| | 0.5 | 85.0 | ″ |
| | 0.1 | 77.5 | ″ |
| No.44 | 1.0 | 100 | ″ |
| | 0.5 | 97.5 | ″ |
| | 0.1 | 95.0 | ″ |
| No.45 | 1.0 | 100 | ″ |
| | 0.5 | 97.5 | ″ |
| | 0.1 | 92.5 | ″ |
| No.46 | 1.0 | 100 | ″ |
| | 0.5 | 100 | ″ |
| | 0.1 | 95.0 | ″ |
| No.47 | 1.0 | 100 | ″ |
| | 0.5 | 95.0 | ″ |
| | 0.1 | 83.3 | ″ |
| No.48 | 1.0 | 100 | ″ |
| | 0.5 | 100 | ″ |
| | 0.1 | 92.5 | ″ |
| No.49 | 1.0 | 100 | ″ |
| | 0.5 | 100 | ″ |
| | 0.1 | 100 | ″ |
| No.50 | 1.0 | 100 | ″ |
| | 0.5 | 100 | ″ |
| | 0.1 | 100 | ″ |

Table 5-continued

| Germicidal ingredient | | Concentration (%) | Normally grown seedling rate (%) | (Chemical injury) Phytotoxicity |
|---|---|---|---|---|
| | No.51 | 1.0 | 100 | " |
| | | 0.5 | 100 | " |
| | | 0.1 | 100 | " |
| | No.52 | 1.0 | 100 | " |
| | | 0.5 | 100 | " |
| | | 0.1 | 100 | " |
| Benlate wettable | | 1.0 | 97.5 | " |
| powder | | 0.5 | 77.5 | " |
| 50% | | 0.1 | 45.0 | " |
| Non-treated pot | | — | 0.0 | " |

Benlate: Methyl-1-(butylcarbamoyl)-2-benzimidazolyl carbamate

EXPERIMENT 6

Slurry treating method

Each wettable powder prepared as "Composition No. 2" was diluted with water to prepare a solution containing 25,000, 10,000 and 5,000 ppm of the active ingredient.

2 ml of the solution was mixed with 100 g of cotton seeds and the mixture was stirred to coat the active ingredient uniformly onto the seeds. The concentration of the active ingredient on the cotton seeds was 0.05, 0.02, 0.01%. *Rhizoctonia Solani* cultured on wheat bran culture was diluted 40 times with soil. The *Rhizoctonia Solani*-containing soil was placed in each pot, of 15 cm diameter, and 20 treated cotton seeds were placed in the soil.

The pot was kept in a green house until the two-leaf stage and then it was kept in a plant room at 25°C in a specific humidity (90%) for 2 days. The number of normally grown seedlings was counted as shown in Experiment 5. Three pots were used for one test.

Table 6

| Germicidal ingredient | | Concentration (%) | Normally grown seedling rate (%) | (Chemical injury) Phytotoxicity |
|---|---|---|---|---|
| Compound | No.2 | 0.05 | 100 | None |
| | | 0.02 | 100 | " |
| | | 0.01 | 100 | " |
| | No.16 | 0.05 | 100 | " |
| | | 0.02 | 100 | " |
| | | 0.01 | 100 | " |
| | No.26 | 0.05 | 100 | " |
| | | 0.02 | 100 | " |
| | | 0.01 | 96.7 | " |
| | No.27 | 0.05 | 100 | " |
| | | 0.02 | 100 | " |
| | | 0.01 | 100 | " |
| | No.31 | 0.05 | 100 | " |
| | | 0.02 | 100 | " |
| | | 0.01 | 100 | " |
| | No.32 | 0.05 | 100 | " |
| | | 0.02 | 96.7 | " |
| | | 0.01 | 86.7 | " |
| Benlate 50% wettable powder | | 0.05 | 66.7 | " |
| (methyl-1-(butylcarbamoyl)- | | 0.02 | 33.3 | " |
| 2-benzimidazolyl carbamate) | | 0.01 | 13.3 | " |
| Captan 50% wettable powder | | 0.05 | 43.3 | " |
| N-trichloromethyl thio-4- | | 0.02 | 16.7 | " |
| cyclohexane-1,2-dicarboximide) | | 0.01 | 3.3 | " |
| TMTD wettable powder | | 0.05 | 46.7 | " |
| (bis(dimethylthiocarbamoyl) | | 0.02 | 16.7 | " |
| disulfide) | | 0.01 | 6.7 | " |
| Non-treated pot | | | 0 | — |

Having now fully described the invention, it will be apparent to one skilled in the art that many changes and modifications can be made thereto without departing from the spirit or scope of the invention as set forth herein.

What is claimed as new and intended to be covered by Letters Patent is:

1. A 2,4-dimethyl-3-carboxyanilido-furan compound of the formula

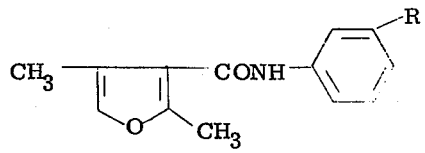

wherein R is $C_{1-10}$ alkyl, $C_{1-10}$ alkoxy, $C_{3-10}$ alkenyloxy or $C_{3-10}$ alkynyloxy.

2. The compound of claim 1 which is 2,4-dimethyl-3-(3-methylcarboxanilido)-furan.

3. The compound of claim 1 which is 2,4-dimethyl-3-(3-methoxycarboxanilido)-furan.

4. The compound of claim 1 which is 2,4-dimethyl-3-(3-ethoxycarboxanilido)-furan.

5. The compound of claim 1 which is 2,4-dimethyl-3-3-isopropoxycarboxanilido)-furan.

6. The compound of claim 1 whichis 2,4-dimethyl-3-(3-allyloxycarboxanilido)-furan.

7. The compound of claim 1 which is 2,4-dimethyl-3-(3-propargyloxycarboxanilido)-furan.

8. The compound of claim 1 which is 2,4-dimethyl-3-(3-ethylcarboxanilido)-furan.

* * * * *